US012661362B2

(12) United States Patent
Zuo et al.

(10) Patent No.: US 12,661,362 B2
(45) Date of Patent: Jun. 23, 2026

(54) METHODS FOR THE PREVENTION AND TREATMENT OF HEARING LOSS

(71) Applicant: Ting Therapeutics LLC, Omaha, NE (US)

(72) Inventors: Jian Zuo, Carlsbad, CA (US); Pezhman Salehi Dermanaki, Elkhorn, NE (US); Marisa Laura Zallocchi, Omaha, NE (US); Sarath Vijayakumar, Omaha, NE (US)

(73) Assignee: Ting Therapeutics, Inc., San Diego, CA (US)

( * ) Notice: Subject to any disclaimer, the term of this patent is extended or adjusted under 35 U.S.C. 154(b) by 39 days.

(21) Appl. No.: 18/081,951

(22) Filed: Dec. 15, 2022

(65) Prior Publication Data

US 2023/0285418 A1    Sep. 14, 2023

Related U.S. Application Data

(63) Continuation of application No. PCT/US2021/041199, filed on Jul. 10, 2021.

(60) Provisional application No. 63/050,568, filed on Jul. 10, 2020.

(51) Int. Cl.

| | |
|---|---|
| *A61K 31/165* | (2006.01) |
| *A61F 11/00* | (2022.01) |
| *A61K 31/122* | (2006.01) |
| *A61K 31/167* | (2006.01) |
| *A61K 31/397* | (2006.01) |
| *A61K 31/506* | (2006.01) |
| *A61K 31/513* | (2006.01) |
| *A61K 31/517* | (2006.01) |
| *A61K 31/5377* | (2006.01) |
| *A61K 31/609* | (2006.01) |
| *A61K 31/7036* | (2006.01) |
| *A61K 33/243* | (2019.01) |
| *A61K 45/06* | (2006.01) |
| *A61P 27/16* | (2006.01) |

(52) U.S. Cl.
CPC .......... *A61K 31/5377* (2013.01); *A61F 11/00* (2013.01); *A61K 31/122* (2013.01); *A61K 31/165* (2013.01); *A61K 31/167* (2013.01); *A61K 31/397* (2013.01); *A61K 31/506* (2013.01); *A61K 31/513* (2013.01); *A61K 31/517* (2013.01); *A61K 31/609* (2013.01); *A61K 31/7036* (2013.01); *A61K 33/243* (2019.01); *A61K 45/06* (2013.01); *A61P 27/16* (2018.01)

(58) Field of Classification Search
CPC .................................................. A61K 31/165
See application file for complete search history.

(56) References Cited

U.S. PATENT DOCUMENTS

| | | | |
|---|---|---|---|
| 8,420,595 B2 | 4/2013 | Kopke et al. | |
| 9,572,815 B2 | 2/2017 | Zuo et al. | |
| 2004/0110719 A1 | 6/2004 | Campbell | |
| 2008/0280955 A1 | 11/2008 | McCamish | |
| 2013/0085112 A1 | 4/2013 | Collard et al. | |
| 2014/0235631 A1 | 8/2014 | Bunt et al. | |
| 2016/0089371 A1 | 3/2016 | Liu et al. | |
| 2017/0327557 A1 | 11/2017 | Chen | |
| 2018/0161340 A1 | 6/2018 | Zuo et al. | |
| 2020/0093923 A1 | 3/2020 | Zuo et al. | |

FOREIGN PATENT DOCUMENTS

| | | |
|---|---|---|
| WO | 2016114655 A1 | 7/2016 |
| WO | 2018204764 A1 | 11/2018 |

OTHER PUBLICATIONS

Atkinson et al. "hair Cell Regeneration after ATOH1 Gene Therapy in the Cochlea of Profoundly Deaf Adult Guinea Pigs," PLoS ONE, Jul. 18, 2014 (Jul. 18, 2014), vol. 9, Iss. 7, pp. 1-11. entire document.
Boanza et al. "A primary role fo the epidermal growth factor receptor in ommatidial spacing in the *Drosophila* eye," Current Biology, Mar. 20, 2001 (Mar. 20, 2001), vol. 9, Iss. 6, pp. 396-404. entire document.
Dabestani et al, Drug Repurposing of an EGF Inhibitor for Protection Against Noise-Induced Hearing Loss. 2020. Creighton University, M.Sc. Thesis. ProQuest, PQ No. 28001904; http://hld.handle.net/10504/127028.
Jarman et al. "The role of Atonal transcription factors in the development of mechanosensitive cells," Seminars in Cell and Developmental Biology, May 1, 2013 (May 1, 2013), vol. 24, Iss. 5, pp. 438-447. entire document.
McDowell, Brian. International Preliminary Report on Patentability. PCT. Jun. 17, 2022. 1-15.
McDowell, Brian. International Search Report of the ISA. PCT. Nov. 15, 2021. 1-2.
Rodriquez, Kari. Written Opinion of the ISA. PCT. Nov. 15, 2021. 1-4.
Teitz et al., "CDK2 inhibitors as candidate therapeutics for cisplatin- and noise-induced hearing loss," J. Exp. Med. Apr. 2, 2018, vol. 215, No. 4, pp. 1187-1203.

(Continued)

*Primary Examiner* — Brian E Mcdowell
(74) *Attorney, Agent, or Firm* — Susan B. Fentress; Veritay Group IP PLLC

(57) ABSTRACT

Acquired hearing loss due to chemotherapy or noise exposure is a major health problem, and Cisplatin chemotherapy often causes permanent hearing loss in cancer patients. However, there are no FDA-approved drugs for the treatment or prevention of Cisplatin- or noise-induced hearing loss. In one aspect, use of Niclosamide, Ingenol, and Elesclomol as an active agent to treat a hearing impairment and to prevent a hearing impairment, and methods of treating and/or preventing hearing impairments or disorders using the compositions are disclosed. This abstract is intended as a scanning tool for purposes of searching in the particular art and is not intended to be limiting of the present invention.

1 Claim, 12 Drawing Sheets

Specification includes a Sequence Listing.

(56)  References Cited

OTHER PUBLICATIONS

Lee et al "Ezetimibe, an NPC1L1inhibitor, is a potent Nrf2 activator that protectsmice from diet-induced nonalcoholic steatohepatitis" Free Rad/ Bio. and Med. V. 99 520-532 (2016).

Zhang et al. "NRF2 activation protects Auditory Hair cells from Cisplatin-Induced Ototoxicity Independent on Mitochondrial ROS production" Toxi. Lett. V. 331 (2020).

Li, R. et al. "Niclosamide Overcomes Acquired Resistance to Erlotinib Through Suppression of STAT3 in Non-Small Cell Lung Cancer" Mol. Can. Ther. V. 12 (10) pp. 2200-2212 ( 2013).

Salehi, p et al. "In Silico Transcriptomics Identifies FDA-Approved Drugs and Biological Pathways for Protection Against Cisplatin-Induced Hearing Loss" BioRxiv pp. 1-66 ( Jan. 18, 2022).

Vijayakumar, S. et al. "In Silico Transcriptome Screens Identify Epidermal Growth Factor Receptor Inhibitors as Therapeutics For Noise-Induced Hearing Loss" Sci. Adv. V. 10. pp. 1-19 ( 2024).

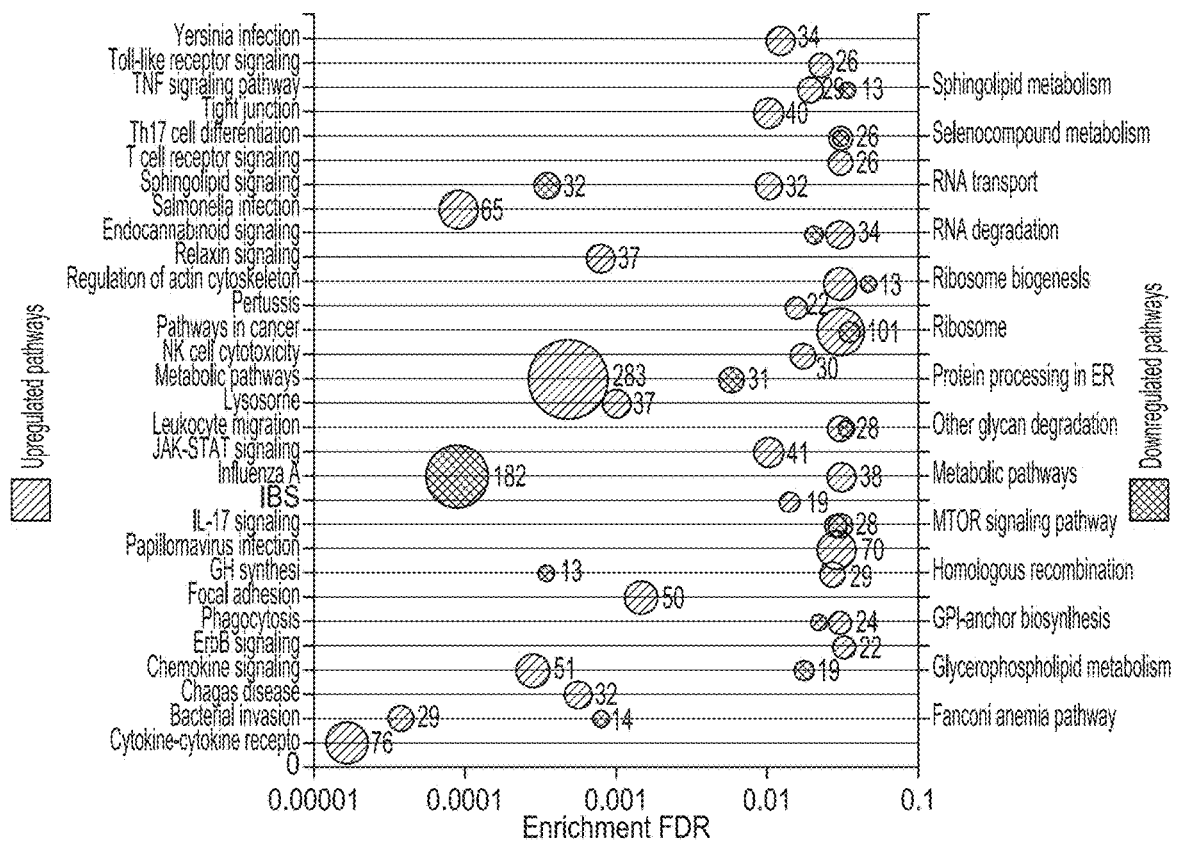

FIG. 2A

| Rank | Drug | Up | Down | Rank | Drug | Up | Down | Rank | Drug | Up | Down |
|------|------|-----|------|------|------|-----|------|------|------|-----|------|
| 1 | Niclosamide | 367 | 181 | 11 | Triptolide | 289 | 166 | 21 | Palbociclib | 11 | 4 |
| 2 | Vorinostat | 356 | 141 | 12 | Camptothecin | 284 | 185 | 22 | Importazole | 8 | 9 |
| 3 | 6 Mercapropurine | 348 | 141 | 13 | Irinotecan | 271 | 126 | 23 | Rottlerin | 8 | 3 |
| 4 | Dasatinib | 329 | 215 | 14 | Cucurbitacin A | 257 | 161 | 24 | Chaetocin | 7 | 3 |
| 5 | Raltitrexed | 329 | 154 | 15 | Thioridazine | 253 | 168 | 25 | Prothionamide | 4 | 2 |
| 6 | Everolinus | 327 | 209 | 16 | Ingenol | 17 | 4 | 26 | Radicicol | 4 | 4 |
| 7 | Elesclomol | 324 | 129 | 17 | Ixazomib | 13 | 3 | 27 | Wortmanin | 4 | 6 |
| 8 | 5FU | 317 | 129 | 18 | Perhexine maleate | 13 | 1 | 28 | Parthenolide | 3 | 0 |
| 9 | Emetine | 303 | 140 | 19 | Salermide | 13 | 7 | 29 | Succimer | 2 | 0 |
| 10 | L-cysteine | 301 | 196 | 20 | Manumycin A | 11 | 4 | 30 | DCPIB | 0 | 2 |

FIG. 2B

Ingenol

SEQUENCE LISTING

```
Sequence total quantity: 1
SEQ ID NO: 1            moltype = DNA   length = 25
FEATURE                 Location/Qualifiers
misc_feature            1..25
                        note = synthetic Danio rerio
source                  1..25
                        mol_type = other DNA
                        organism = synthetic construct
SEQUENCE: 1
catttcaatc tccatcatgt ctcag                                        25
```

METHODS FOR THE PREVENTION AND TREATMENT OF HEARING LOSS

CROSS-REFERENCE TO RELATED APPLICATIONS

This application is a continuation of PCT/US21/41199 and claims the benefit of U.S. provisional patent application Ser. No. 63/050,568 filed Jul. 10, 2020, under 35 USC § 119(e) and 35 U.S.C. § 111(a) (hereby specifically incorporated herein by reference).

STATEMENT REGARDING FEDERALLY SPONSORED RESEARCH OR DEVELOPMENT

This invention was made with government support under Grant Numbers 1 R43 DC018762, R01 DC015444, R01 DC015010 awarded by the National Institutes of Health National Institute on Deafness and Other Communication, Grant Numbers N00014-18-1-2507 awarded by the Office of Naval Research, and Grant Numbers USAMRMC-RH170030 Awarded by the Department of Defense. The government has certain rights in the invention.

REFERENCE TO A "SEQUENCE LISTING

Applicant hereby specifically incorporates by reference the files PATENTIN_ST25, created on Apr. 19, 2023 and of 346 MB

BACKGROUND OF THE INVENTION

(1) Field of the Invention

The present invention relates to therapeutic uses of Niclosamide, for treating, inhibiting, and/or preventing loss of hearing.

(2) Description of Related Art Including Information Disclosed Under 37 CFR 1.97 and 37 CFR 1.98

Acquired hearing loss due to chemotherapy or noise exposure is a major health problem and Cisplatin chemotherapy often causes permanent hearing loss in cancer patients. However, there are no FDA-approved drugs for the treatment or prevention of Cisplatin- or noise-induced hearing loss. Platinum-based chemotherapy is a standard of care for various types of cancers, including ovarian, lung, testicular, and head and neck carcinoma. Cisplatin, one of the most effective platinum compounds, causes permanent hearing loss in 40-60% of treated cancer patients. One of the known mechanisms of Cisplatin damage to the auditory sensory cells is DNA adduct formation leading to oxidative stress and cellular apoptosis. To reduce Cisplatin damage to the inner ear cochlear cells, various therapeutic strategies including usage of antioxidants, anti-inflammatory agents, calcium channel blockers, kinase inhibitors, heat shock proteins, and thiol compounds as chemical deactivators have been used in previous studies. Sodium thiosulfate (STS), for example, has been shown effective in protecting hearing only in pediatric patients with localized hepatoblastoma who received Cisplatin chemotherapy; however, it acts as a Cisplatin chelator and is ineffective in protecting Cisplatin-induced hearing loss (CIHL) in patients with other cancers.

There exists a need in the art for a solution to hearing loss due to noise, antibiotics, Cisplatin during chemotherapy, or aging. Therapeutic methods described are a solution to problems in the art such as narrow therapeutic windows and safety margins and interference with Cisplatin's antineoplastic activity.

BRIEF SUMMARY OF THE INVENTION

The invention provides a method to prevent or treat hearing loss including the steps of: administering to an animal in need thereof an effective amount of a pharmaceutical composition containing a therapeutically active agent, wherein the therapeutically active agent includes: Niclosamide, Ingenol, and Elesclomol.

The inventive subject matter also includes a composition for use in preventing or treating hearing loss by protecting inner ear cells from death wherein said composition is an effective amount of: an active agent, wherein the active agent is selected from the group including: Niclosamide, Ingenol, and Elesclomol or a pharmaceutically acceptable salt thereof.

The inventive subject matter also includes a kit made of: an active agent, wherein the active agent is selected from the group consisting of: Niclosamide, Ingenol, and Elesclomol or a pharmaceutically acceptable salt thereof; and one or more of: (A) at least one chemotherapeutic agent; at least one antibiotic inhibitor and (C) instructions for preventing a hearing impairment.

BRIEF DESCRIPTION OF THE SEVERAL VIEWS OF THE DRAWING

The accompanying figures, which are incorporated in and constitute a part of this specification, illustrate several aspects and together with the description serve to explain the principles of the invention.

FIG. 2A-2B show transcriptome analysis of cisplatin-resistant cancer cell lines reveals implicated pathways and shared gene targets with identified drugs. A) Pooled cancer cell line profiles available from GEO database were analyzed using GSEA to identify enriched molecular pathways from the KEGG database. Upregulated pathways are shown in red on the left, while downregulated pathways are shown in blue on the right. Circle size is correlated to the number of the genes mapped to its respective FDR value. B) Gene expression profiles for each drug derived from the iLINCS database were compared to those differentially expressed genes identified by GSEA. Overlapping genes in the same direction were then used to rank drugs.

DETAILED DESCRIPTION OF THE INVENTION

The present invention can be understood more readily by reference to the following detailed description of the invention and the Examples included therein. Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

In one aspect, compounds can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss. Therapeutic agent means a chemical substance that is used for the treatment or mitigation of a disease condition or ailment.

Figure 1:
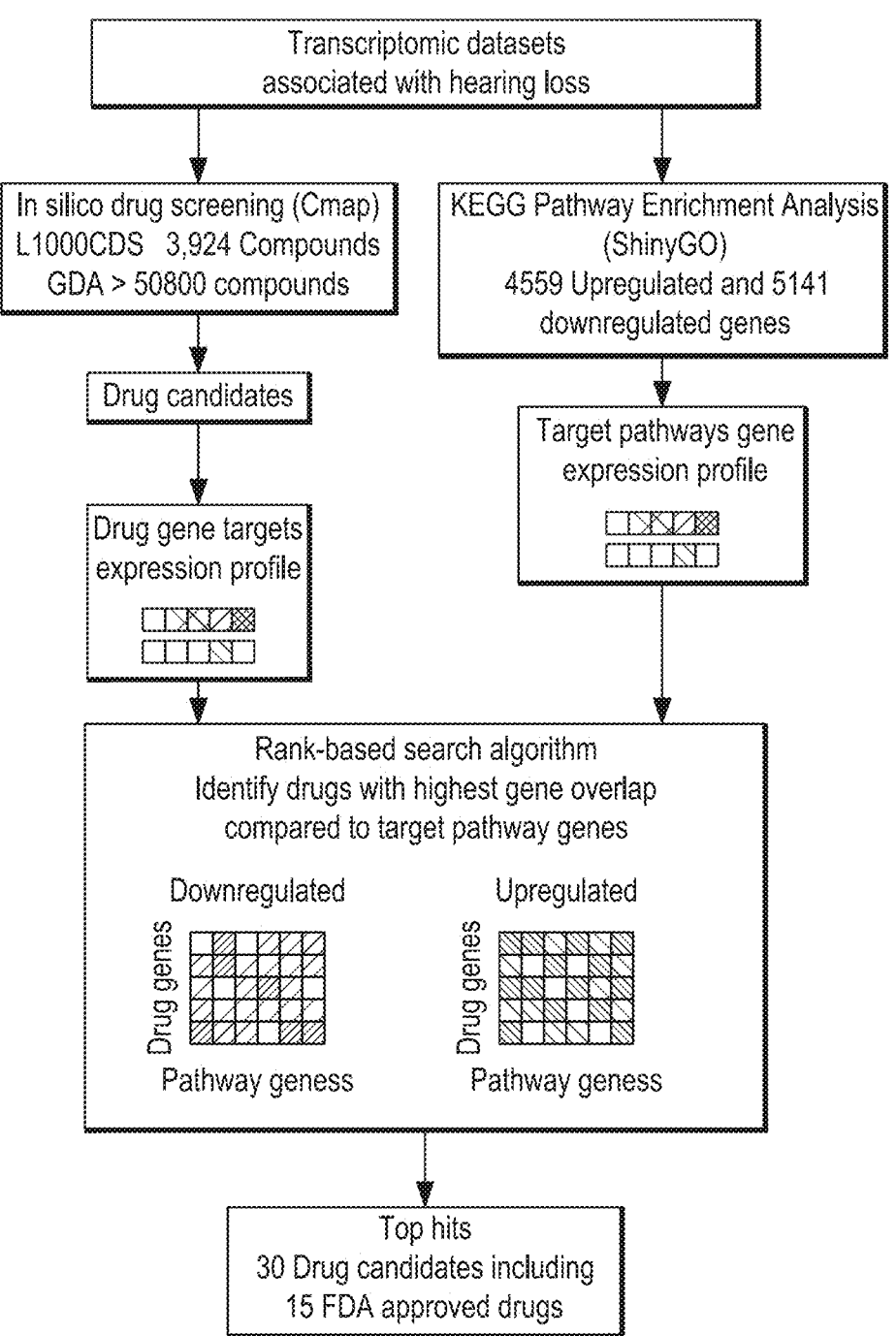
FIG. 1 is a schematic diagram showing how compounds of this invention were identified based on a comparison of data sets from drug screen connectivity maps and pathway enrichment analysis reveal drugs acting against hearing loss. Transcriptomic profiles of cisplatin resistant cancer cell lines and their parental cisplatin sensitive cells were analyzed using the L1000CDS2 and GDA drug-gene interaction databases. The differentially expressed genes of each compound were then compared to those differentially expressed genes identified using KEGG pathway enrichment analysis of the original GEO profiles to find overlapping genes implicated in cisplatin resistance. Of the original 50 drugs, 30 were validated both in vitro and in vivo, with niclosamide emerging as the top-hit compound.

Now referring to FIGS. 1 and 2A-2B compounds were identified based on a comparison of data sets from drug screen connectivity maps and pathway enrichment analysis revealing compounds acting against hearing loss. This method was developed to derive drug candidates from a diverse chemical space, covering a wide range of biological pathways, avoiding bias associated with focusing on previously reported pathways. The resulting compounds exhibited overlaps in gene expression transcriptomic profiles between at least one of a plurality of cell-lines or mouse strains treated with ototoxic insults (cisplatin, noise, or antibiotic exposure Cisplatin (FIGS. 5A/5D, noise (FIG. 5B), and antibiotics (FIG. 5C) and at least one of a plurality of cell-lines or mouse strains treated with one of the compounds. Here specifically, the data set sought was conformity to a NIHL-resistant mouse strains to NIHL sensitive mouse strains (129SvJ and CAST). Here specifically and in addition, the data set sought was conformity to cisplatin-resistant and sensitive cancer cell lines, HEI-OC1 cell line, and in vivo mouse cochlear single cell RNA seq with and without cisplatin treatment. Here again, additionally used, were transcriptome perturbation of neonatal mouse organ of *Corti* exposed to gentamicin for damage related to antibiotic treatment. The compounds with an overlap from the results of the computations from these data sets include but are not limited to: Niclosamide, Ingenol, and Elesclomol.

Now referring to FIGS. 2A-2B, transcriptome analysis of cisplatin-resistant cancer cell lines reveals implicated pathways and shared gene targets with identified drugs. A) Pooled cancer cell line profiles available from GEO database were analyzed using GSEA to identify enriched molecular pathways from the KEGG database. Upregulated pathways are shown in red on the left, while downregulated pathways are shown in blue on the right. Circle size is correlated to the number of the genes mapped to its respective FDR value. B) Gene expression profiles for each drug derived from the iLINCS database were compared to those differentially expressed genes identified by GSEA. Overlapping genes in the same direction were then used to rank drugs.

Niclosamide, a previously FDA-approved drug widely used for treating tapeworm infections since 1982, exhibits excellent protection against Cisplatin-induced hearing loss in zebrafish and mice when administered prophylactically. Niclosamide, also demonstrates protection against kainite acid-induced hair cell loss in zebrafish and noise-induced hearing loss in mice. Together, these data show that Niclosamide can be repurposed as an otoprotectants against Cisplatin and noise injuries. In one aspect, Niclosamide can be used as a therapy for the treatment and/or prevention of hearing loss. In various aspects, the compounds and compositions of the invention can be administered in pharmaceutical compositions, which are formulated according to the intended method of administration. The compounds of this invention are defined as a therapeutically active agent in a treatment regimen or procedure that is intended for preventing hearing loss by noise or aging by protecting inner ear cells from death and in preventing hearing loss by chemotherapy or antibiotics induced hearing loss. Therapeutic agent means a chemical substance that is used for the treatment or mitigation of a disease condition or ailment.

Niclosamide is revealed to protect against hair cell apoptosis. Niclosamide is identified as acting against hair cell loss in animals by the models and data presented. Models reveal properties necessary for an otoprotective compound such as high efficacy against hair cell loss, relatively low toxicity, lack of metal chelating and blood-brain-barrier permeability. Niclosamide, is revealed to have high efficacy and high affinity in mouse and zebrafish models used to demonstrate protection against hair cell loss. The lateral-line neuromasts of zebrafish are a valuable model for testing compounds protective against Cisplatin toxicity in vivo, as their HCs are considered homologous to those in the mammalian inner ear and are readily accessible to drugs in vivo. Teitz et al., J. Exp. Med. 2; 215(4):1187-1203 (2018) Mouse models involving HEI-OC1 have shown effective in validating therapeutic uses of compounds against hearing loss due to Cisplatin, noise, antibiotics, and aging. Teitz et al., J. Exp. Med. 2; 215(4):1187-1203 (2018).

The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration. Niclosamide, can be synthesized by a variety of methods known in the art. Jayaprakash, V. et al., Medicinal Chemistry of Neglected and Tropical Diseases: Advances in the Design and Synthesis of Antimicrobial Agents. United States, CRC Press, 2019. p. 348. RC961.M467.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, PA 1990.

In various aspects, the disclosed pharmaceutical compositions include the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

In preparing the compositions for oral dosage form, any convenient pharmaceutical media can be employed. The pharmaceutical compositions of the present invention include a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

The following are intended to be exemplary of how one of ordinary skill in the art could make and evaluate the claimed methods compounds, compositions, articles, and/or devices, and are not intended to limit the scope of the invention.

In various aspects, these compounds, such as Niclosamide, can be used in combination with one or more other drugs, in the form of a kit, to prevention, control, amelioration, or reduction of risk of hearing impairments, when the other drugs can have been known to impair hearing.

Figures 3A, 3B:
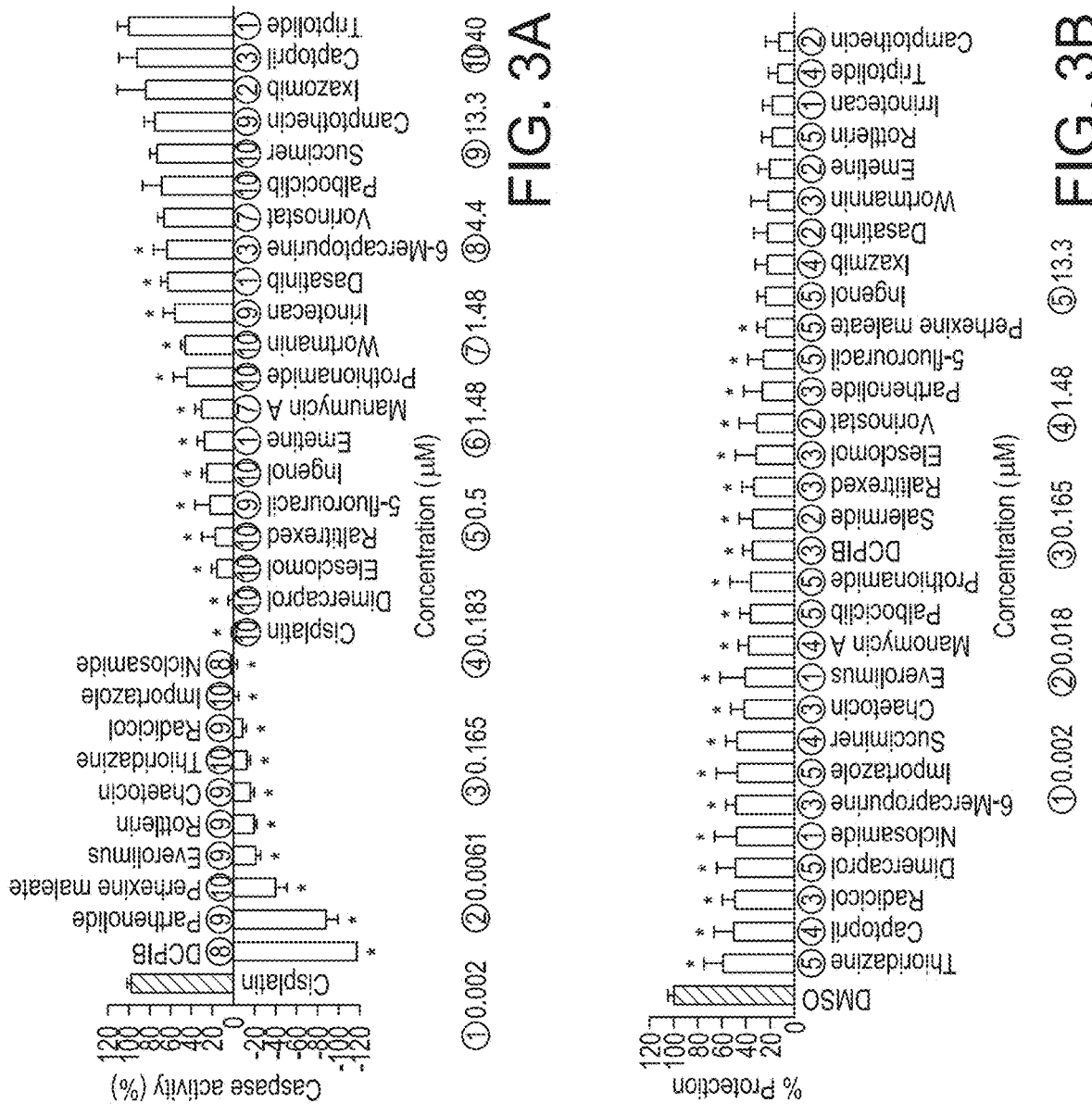
FIG. 3A-3F shows Niclosamide's protection against hearing loss. A) Lowest level of caspase-3/7 activity in HEI-OC1 cells treated with Cisplatin (50 µM) and experimental compounds. Raw caspase reads were normalized to caspase activity in cells treated with Cisplatin/DMSO and cells treated with 1% DMSO. Niclosamide, was shown to reduce caspase activity to comparable levels as control cells at a dose of 4.4 µM. Data are shown as mean±standard error (n=3 wells per treatment). *P<0.05 (One Way ANOVA). B) Highest level of protection in zebrafish treated with Cisplatin and experimental compounds quantified by neuromast count hair cell count. Quantification of the HCs at S03 (supraorbital line neuromast) and 01-2 (Otic line neuromasts) revealed significantly reduced Cisplatin damage in zebrafish HCs pretreated with 0.002 µM Niclosamide, (n=5 to 8 per group, One Way ANOVA). C) Fluorescent staining of zebrafish neuromasts treated with vehicle (DMSO), Cisplatin and Cisplatin+Niclosamide, (0.002 µM to 13.3 µM). D) The dose response curve of Niclosamide with Cisplatin exposure in HEI-OC1 cells. E) The dose response curve of Niclosamide without Cisplatin exposure in HEI-OC1 cells. F) Highest level of protection in zebrafish treated with Cisplatin and experimental compounds quantified by hair cell count per neuromast. Quantification of the HCs at S03 (supraorbital line neuromast) and 01-2 (Otic line neuromasts) revealed significantly reduced Cisplatin damage in zebrafish HCs pretreated with 0.002 µM Niclosamide, (n=5 to 8 per group, One Way ANOVA).
Figure 3C:
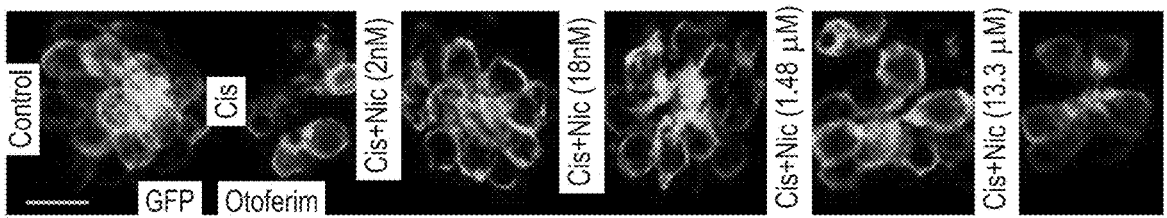
Figure 3D:
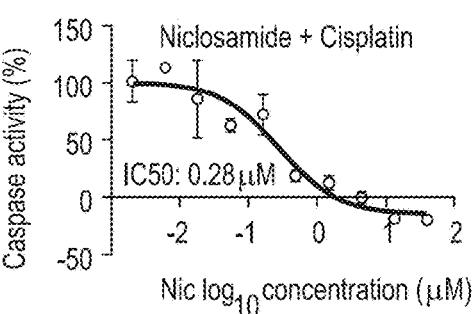
Figure 3E:
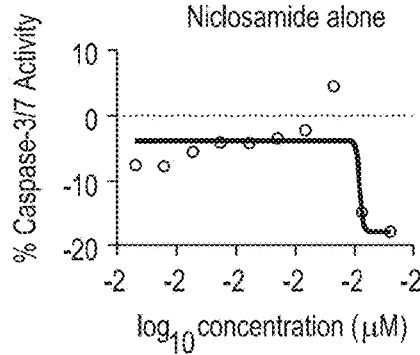

Now referring to FIG. 3A, and FIGS. 3D-3E, compounds protect from cisplatin toxicity in the mouse inner ear cell line. House Ear Institute-Organ of *Corti* 1 (HEI-OC1) cells (House Research Institute) were maintained in high-glucose Dulbecco's modified Eagle medium supplemented with 10% fetal bovine serum (Life Technologies, USA) at 33° C. and 10% $CO2$ as previously described (Kalinec et al., 2003). Cells were seeded at 8,000 cells/well in 96 well plates and left to attach overnight. Now referring to FIG. 3A, For the drug screening, HEI-OC1 cells were pretreated with 30 drug candidates at concentrations ranging from 2 nM to 40 μM one hour before receiving cisplatin. The cisplatin dose (50 μM) was based on our previously published dose response curve. The cells were co-incubated with cisplatin and drug candidates for an additional 19 hours prior to Caspase-Glo 3/7 assay (Promega, Madison, WI) as previously shown. Additionally, DMSO-only cells, and kenpaullone-treated cells were used as positive controls to validate our results. The DMSO concentration in drug preparation was adjusted to 0.1% v/v and it was verified that 0.5% DMSO had no effect on the cell death kinetics (Hall et al., 2014). Results of the assay were run in triplicate and normalized to cisplatin-only and media-only controls. The percent caspase activity was used to determine the relative protective effect of each compound. The luminescence detection representing caspase activity in each well was obtained using a Cytation Hybrid Multi-Mode Reader (Biotek, Winooski, VT, USA). The percent protection of the cells was calculated using caspase 3/7 readouts and the following formula:

$$\text{Percent protection} = 100 - \frac{\text{Drug and Cisplatin exposed} - Cont}{\text{Cisplatin exposed} - Cont} \times 100$$

Now referring to FIG. 3D-3E shows the dose response curve of Niclosamide, with and without Cisplatin exposure in HEI-OC1 cells. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with Niclosamide, reached 0% caspase activity or full protection at a dosage of ~4.4 μM. Additionally, Niclosamide had a relatively low calculated $IC_{50}$ of 280 nM. Niclosamide has a wider therapeutic window, demonstrating some level of protection at over 80% of the dosage range tested. Mice administered Niclosamide, showed no weight loss or abnormal behavior at maximum IP doses approved by IACUC. Mice injected with combination of Cisplatin (30 mg/kg/ single injection) and Niclosamide showed no general toxicity, compared to mice treated with Cisplatin alone. In the following examples, Niclosamide, 5-chloro-N-(2-chloro-4- nitrophenyl)-2-hydroxy-benzamide, with a ≥95% purity was used for all experiments (Cayman Chemical, USA).

The protective effect of Niclosamide in HEI-OC1 cells described above were compared to kenpaullone, a known CDK2 inhibitor that enhances cell survival by reducing Cisplatin-induced mitochondrial ROS production. Kenpaullone's effects in HEI-OC1 cells were previously characterized in Teitz et al., J. Exp. Med. 215(4):1187-1203 (2018). The comparison demonstrates that Niclosamide shows comparable levels of protection to kenpaullone against Cisplatin damage in HEI-OC1 cells, and better protection than four other benchmark compounds (sodium thiosulfate, ebselen, dexamethasone, and N-acetylcysteine).

Figure 3F:
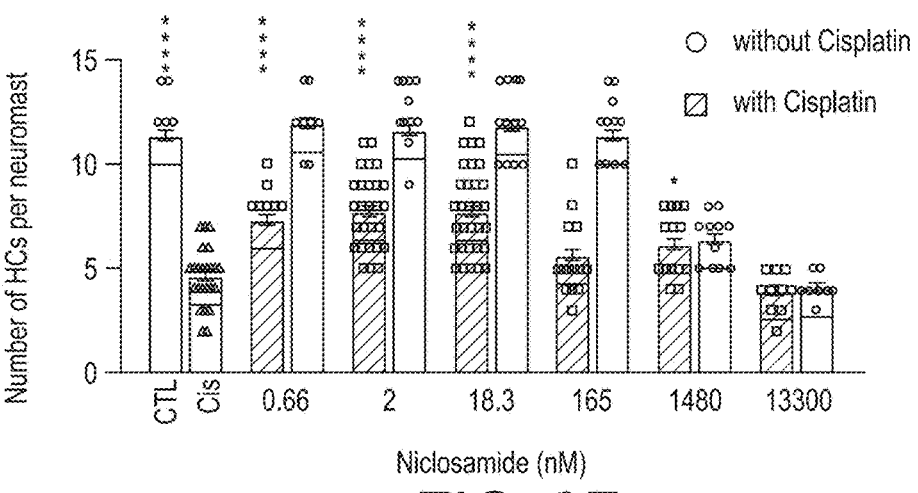

Now referring to FIGS. 3B-3C, and FIG. 3F, highest level of protection in zebrafish treated with Cisplatin and experimental compounds quantified by neuromast count hair cell count. *Danio rerio* experimental larvae were obtained by pair mating of adult fish maintained at Creighton University by standard methods approved by the Institutional Animal Care and Use Committee. The lateral-line neuromasts of zebrafish are a valuable system for testing protectivity of compounds against Cisplatin toxicity in vivo, as their HCs are considered homologous to those in the mammalian inner ear and are readily accessible to drugs. We used Tg(pou4f3: mGFP) expressing a membrane bound GFP in HCs. Experimental fish were maintained at 28.5° C. in E3 media (5 mM NaCl, 0.17 mM KCl, 0.33 mM $CaCl_2$) and 0.33 nM MgSO4, pH 7.2). Animals were cryoanaesthetized after drug treatment and prior to fixation. The neuromasts inspected, S03 and O1-2, were part of the cranial system and included the otic, middle, and opercular neuromasts.

For the screenings, 5-day post-fertilization (dpf) Tg(brn3c:GFP) larvae were pre-incubated with 41 drug candidates at 0.002, 0.018, 0.165, 1.48, and 13.3 µM for 1 hour followed by co-incubation with 400 µM Cisplatin for 4 hours. Subsequently, animals were transferred to E3 water for 5 hours and fixed in 4% paraformaldehyde (PFA) overnight (26). Neuromast HCs were immunolabeled with anti-otoferlin (HCS-1, DSHB) and anti-GFP (NB100-1614, Novus Biologicals). These two markers were used to detect and count neuromast HCs to reduce the chances of missing some of the HCs after the treatment since we previously noticed that incubation with the compounds can affect GFP expression more difficult to detect under a fluorescence microscope. Otic, middle, and opercular neuromasts were identified, and HCs at S03 (supraorbital line neuromast) and O1-2 (Otic line neuromasts) were manually counted using a Zeiss AxioSkop 2 fluorescence microscope with a 40× oil objective. Compounds were then evaluated on efficiency and potency, with the top-rated compounds showing high protection at lower concentrations.

Quantification of the HCs at S03 (supraorbital line neuromast) and O1-2 (Otic line neuromasts) revealed significantly reduced Cisplatin damage in zebrafish HCs pretreated with 0.002 µM Niclosamide, (n=5 to 8 per group, One Way ANOVA). Now referring to FIG. 3F, Quantification of the HCs at S03 (supraorbital line neuromast) and O1-2 (Otic line neuromasts) across multiple doses in zebrafish (n=5-8 per group, One Way ANOVA). *$P<0.05$, data are shown as mean±standard error (n=5 per group). *$P<0.05$, data shown as mean±standard error in all panels.

Now referring to FIG. 3B, Numbers were normalized to those of zebrafish treated exclusively with Cisplatin at 300 µM (as 0% protection) or medium (DMSO; as 100% protection) to generate percent protection for each compound. Drug candidates were ranked based on the most effective dose in prevention of the Cisplatin damage to the neuromast HCs (FIG. 2B). Among 42 top compounds tested, Niclosamide, was found to be most potent drug candidate, providing the highest level of protection (~50%) at the lowest concentration tested (0.002 µM) (FIG. 3B) Maximum protection was achieved at 0.002 µM, suggesting a suitable concentration for in-human use. This concentration being ~9000× lower than human Cmax (18 µM), following 2,000 mg oral use.

Now referring to FIG. 3C fluorescent staining of zebrafish neuromasts treated with Niclosamide. Niclosamide, was shown to reduce hair cell loss at concentrations ranging from 0.002-13.3 µM in zebrafish treated with Cisplatin. GFP is shown in green, and otoferlin is shown in red (n=3 per drug dose, scale bar=20 µm).

Now referring to FIGS. 4A-4F Niclosamide attenuates Cisplatin-induced hearing loss in FVB/NJ mice. Mice: Procedures used with mice were approved by the Institutional Animal Care and Use Committee (IACUC) at the Creighton University. For functional assessments including Cisplatin and noise exposure experiments 5 to 7-week-old FVB/NJ mice obtained from Jackson Laboratory (Bar Harbor, ME, USA) were used, with a mix of males and females across experiments. For the Cisplatin and noise studies, FVB/NJ mice were treated with 10 mg/kg Niclosamide, through intraperitoneal (IP) injection. Niclosamide, was dissolved in 1% DMSO in normal saline (0.9% NaCl solution) and vortexed multiple times before injections. Treatment started 24 hours before the Cisplatin or noise-exposure and continued once daily for 3 more days. Cisplatin was injected IP at 30 mg/kg divided into 2 doses per day. Animals were given 1 mL warm sterile normal saline subcutaneously twice a day before and for 7 days after Cisplatin treatment to prevent dehydration.

Figure 4A:
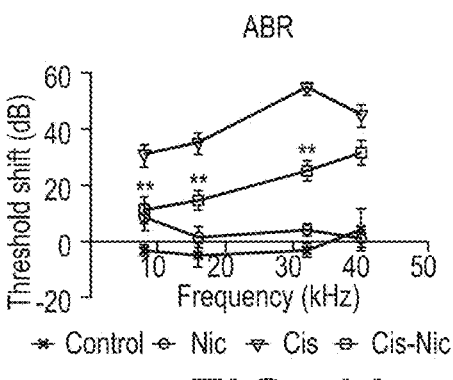
FIG. 4A-4F shows Niclosamide demonstrates otoprotective effects against Cisplatin in vivo. A) Niclosamide showed significantly reduced ABR threshold shifts at 8, 12, and 32 kHz as compared to Cisplatin-only treated mice (n=8 per group, Two Way ANOVA). B) Niclosamide showed significantly reduced DPOAE threshold shifts at 16 and 32 kHz as compared to Cisplatin-only treated mice (n=8 per group, Two Way ANOVA). C, D) Wave I amplitudes at baseline showed no differences across all four groups. After Cisplatin exposure, Niclosamide was found to increase wave I amplitudes from 8-32 kHz as compared to Cisplatin-only treated mice (n=8 per group, One Way ANOVA). E) Immunofluorescent images of cochlea stained with Myosin 6 (red) and DAPI (blue) at 32 kHz region shows minimal levels of hair cell loss when cotreated with Cisplatin and Niclosamide. Niclosamide was shown to protect against Cisplatin-induced hair cell loss. F) Quantification outer hair cells from immunofluorescent images shows that cotreatment with Niclosamide grants full protection against Cisplatin-induced hair cell lost (n=5 per group, student's t-test). *P<0.05, data shown as mean±standard error in all panels.

Now referring to FIG. 4A, ABR tests were performed 2-3 days before Cisplatin exposure, and 5 days post-Cisplatin exposure. The experimental groups included: Cisplatin and 1% DMSO, Cisplatin and Niclosamide, Niclosamide, only, and age-matched controls receiving normal saline. For the noise experiment, auditory tests were performed 2-3 days prior to noise exposure (paradigm described below), at post-exposure day-1 to monitor temporary threshold shift (TTS) and at post-exposure day-14 to monitor permanent threshold shift (PTS). Experimental groups included: noise-exposure and normal saline, noise-exposure and Niclosamide, Niclosamide-only, and age-matched controls. Following the final auditory function measurements, mice were euthanized, and cochleae were collected for morphological assessment. Based on the results of FVB/NJ ABR/DPOAE threshold variances and power analysis, ten FVB/NJ mice per group (5 of each sex) were used in this study.

To investigate the drugs' effects on mammalian auditory function in vivo, we first treated 5-7 weeks old FVB/NJ mice with four drug candidates: Niclosamide (10 mg/kg/day), Ingenol (0.3 mg/kg/day), Elesclomol (5 mg/kg/day), for 4 consecutive days (IP) to monitor safety of the drugs. All tested doses were determined based on previous published data showing maximum non-toxic dose through intraperitoneal (IP) injection. None of the mice showed reduced weight loss or signs of pain and distress at given doses. Mice treated with Niclosamide, at 20 mg/kg/day (IP) for 4 consecutive days showed sign of pain and distress including mouse hunch and 20-30% weight loss, therefore, 10 mg/kg/day was the maximum dose used in this study.

Baseline auditory brainstem response (ABR) were measured on 16 mice divided in 3 groups receiving Ingenol, Elesclomol, and Niclosamide. The mice received the drug doses described above, then on day 2 of drug injection mice also received 30 mg/kg Cisplatin (IP; 4 mice per group). Daily monitoring showed more than 20% weight loss in mice receiving Ingenol and Elesclomol and we observed 40-60% mortality by day 5 post-treatment in mice receiving these drugs. Mice treated with Cisplatin alone showed 10-15% weight loss. However, the Niclosamide, treated mice showed less than 10% weight loss and all survived through the second ABR test on day 5 post-Cisplatin injection.

Figure 4B:
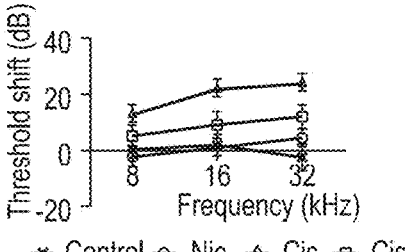

Now referring to FIG. 4B measurement of the distortion products otoacoustic emission (DPOAE) thresholds at frequencies ranging from 8 to 40 kHz in cisplatin, niclosamide, control, and cisplatin-niclosamide treated-mice. The control group's DPOAE thresholds were significantly lower than the Cisplatin treated group at Day 5 post-Cisplatin injection. The results of the 2-way ANOVA followed by post-hoc Tukey's test showed statistically significant differences between Cisplatin-Niclosamide, treated mice and Cisplatin alone group at 16 kHz and 32 kHz.

Figure 4C:
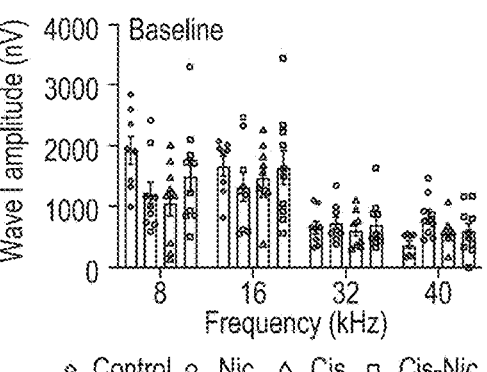
Figure 4D:
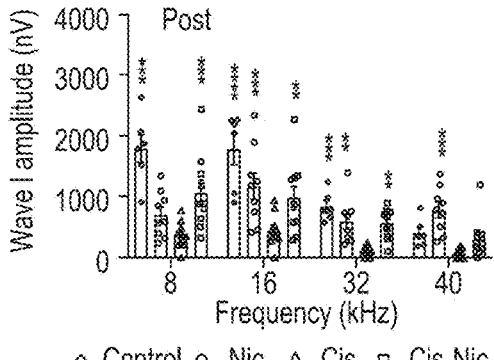

Now referring to FIG. 4C-4D, mean wave-1 amplitudes at 8, 16, 32, and 40 kHz was measured in the control and Niclosamide-treated mice before Cisplatin injection and at Day 5 post-Cisplatin injection. The ABR wave-1 amplitude represents the summed activity of the cochlear nerve. Amplitudes from the 85 dB SPL stimuli were compared between groups in the baseline ABR measurements using a two-factor ANOVA (group x frequency), and no group differences were detected (P>0.05). At Day 5 post-Cisplatin injection, the two-factor ANOVA revealed a significant two-way interaction of group x stimulus level and the post-hoc Tukey's test revealed that the Cisplatin-Niclosamide, treated group had higher amplitudes compared to Cisplatin only group across all tested frequencies at 85 dB SPL (FIGS. 4C,4D).

Figure 4E:
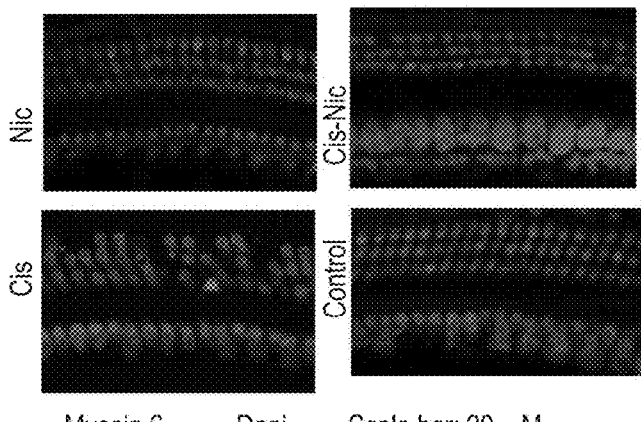
Figure 4F:
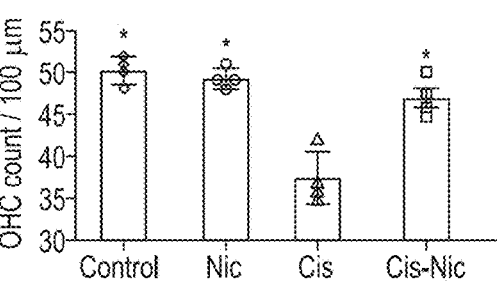

Now referring to FIGS. 4E-2F, representative samples of the mouse HCs at 32 kHz, the most protected frequency region shown by ABR measurement (FIG. 4E). Quantitative data for HC count are displayed in FIG. 4F. The one-way ANOVA revealed a significant group effect (P<0.05). The post-hoc test at each frequency revealed that the Cisplatin-Niclosamide group had more HC survival than the Cisplatin group at the 30 kHz region. These data confirm Niclosamide, protects OHCs against Cisplatin damage. Niclosamide protects NMDA-induced hair cell loss in zebrafish. Application of the N-methyl-d-aspartate (NMDA) to zebrafish neuromast HCs has also been used to mimic glutamate excitotoxicity associated with noise exposure (Katie S. Kindt and Lavinia Sheets, 2018). The results of the HC count following exposure of zebrafish to 300 μM NMDA led to hair-cell loss. However, pretreatment with 2 nM and 18 nM Niclosamide, prior to Cisplatin exposure significantly increased HC survival compared to Cisplatin-DMSO exposed zebrafish larvae.

Now referring to FIGS. 5A-5F Niclosamide had protective effects on NIHL in Zebrafish and FVB/NJ mice in vivo. CIHL and NIHL share mechanistic commonalities. Now referring to FIG. 5A, to test whether Niclosamide protects HCs from excitotoxic trauma, a zebrafish model that mimics noise damage was employed, Zebrafish were exposed to the ionotropic glutamate receptor agonist, N-methyl-D-aspartate (NMDA), previously shown to cause progressive HC loss in zebrafish lateral-line organs (Sheets, 2017) with or without niclosamide. 5-dpf larvae were preincubated with 300 μM NMDA for 50 min followed by 2 hours incubation with niclosamide at 2 nM and 18.3 nM.

Now referring to FIGS. 5B-5F, mice were injected with 10 mg/kg Niclosamide, per IP injection once per day for four consecutive days: one day before noise exposure (8-16 kHz at 105 dB SPL), the day of the noise exposure, and two days after noise exposure. Control animals received vehicle injections on the same schedule.

Figures 5A, 5B, 5C, 5D:
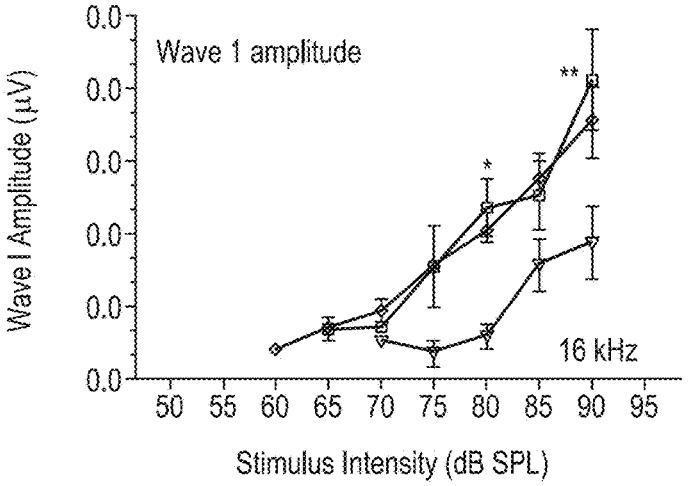
FIG. 5A-5F shows Niclosamide protects against NIHL. A) Niclosamide, reduces NMDA excitotoxicity in zebrafish neuromasts. Hair cell counts were quantified from zebrafish treated with 300 µM NMDA and either 2 or 18.3 nM Niclosamide. At both tested doses, Niclosamide, significantly showed hair cell counts than NMDA-only treated zebrafish. (n=5 per group, One Way ANOVA). B) Niclosamide treated mice with and without noise exposure showed significantly reduced ABR threshold shifts at 8, 12, 32, 40, and 63 kHz as compared to saline+noise treated mice (n=8 per group, Two Way ANOVA). C) There were no differences in DPOAE amplitudes across all groups from 10-80 dB SPL (n=8 per group, Two Way ANOVA). D) Niclosamide treated mice showed comparable wave 1 amplitudes across 65-90 dB SPL to age-matched controls and significantly higher wave I amplitudes at 80- and 90-dB SPL than saline and noise-exposed mice (n=8 per group, One Way ANOVA). E) CtbP2 staining of inner hair cells shows that Niclosamide, protects against synaptic loss in noise exposure (CtbP2 in green). F) Quantification of CtbP2 puncta (Y axis) per inner hair cell (x axis) Mice treated with Niclosamide, were found to have significantly higher synaptic counts than vehicle-treated mice (n=4 per group, student's t-test). *P<0.05, data shown as mean±standard error in all panels.

Now referring to FIG. 5B, Noise-induced ABR threshold shifts were obtained by subtraction of the pre-exposure from the post-exposure thresholds. Two-way ANOVAs at each day revealed significant main effects of group at Day 1. Tukey's multiple comparison test revealed that the Niclosamide-noise exposed group had lower threshold shifts than noise exposed group across all tested frequencies from 8 kHz to 63 kHz at Day 14.

Now referring to FIG. 5C, DPOAE amplitudes were measured at f2 frequency ranging from 10 to 80 dB SPL in mice. For the noise-Niclosamide group, DPOAE amplitudes were significantly higher than the noise-saline group at day-15 post-noise exposure. A two-factor ANOVA (group x frequency) was used to compare pre-exposure amplitudes to Day 15 amplitudes. The ANOVA revealed no significant two-way group x frequency interaction indicating that the OHC function is similar between all groups and Niclosamide's protective effect against noise could be due to prevention of synaptopathy.

Now referring to FIG. 5D, mean wave-I amplitudes at 10, 20, 28.3, and 40 kHz were measured at Day 15 post-noise exposure. Amplitudes from the 10-90 dB SPL stimulus intensity were compared between groups in the pre-noise test using a two-factor ANOVA (group x stimulus level), and no group differences were detected. At Day 15, only the 60-90 dB SPL stimulus levels were used because many of the subjects had no responses below 60 dB SPL. The two-way ANOVA revealed a significant interaction of group x stimulus level (P<0.001). The Tukey's post-hoc revealed that the Niclosamide-noise group had higher amplitudes at 80 and 90 dB SPL compared to noise-exposed group (FIG. 50). The results of the wave-I amplitude showed that cochlear nerve activity in noise-Niclosamide, group was comparable to aged matched controls and there was no statistically significant difference between these groups.

Figure 5E:
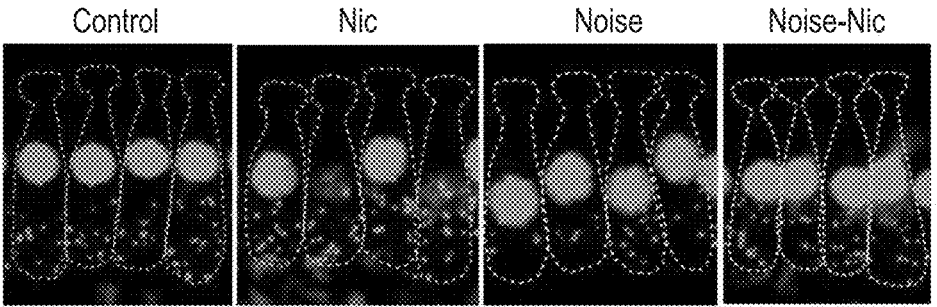
Figure 5F:
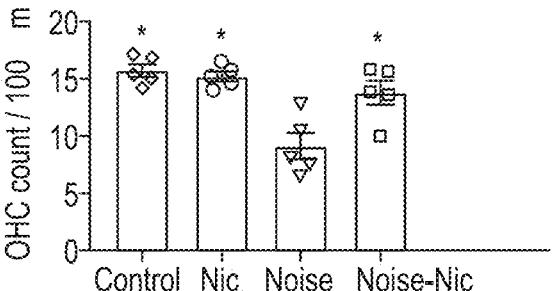

Now referring to FIG. 5E to assess the protection of the ribbon synapses, the cochlear samples were immunostained with CtBP2, one of the most abundant proteins in synaptic ribbon bodies (Kujawa S G, et al. 2006). Representative samples of the mouse ribbon synapses at 16 kHz are displayed. Now referring to FIG. 5F, outer hair cell count of ribbon synapses. Independent samples t-tests at 16 kHz frequency revealed that the Niclosamide-noise group had more synaptic ribbon survival than the saline-noise group. In the same cochleae, OHCs were also counted. Independent samples t-tests at 32 kHz revealed that the proportion of surviving OHCs was similar in the Niclosamide-noise group compared to saline-noise treated animals. The frequency region of 16 kHz was used for CtbP2 ribbon count because this has been shown that ribbons are more abundant in this frequency region.

Figure 6A:
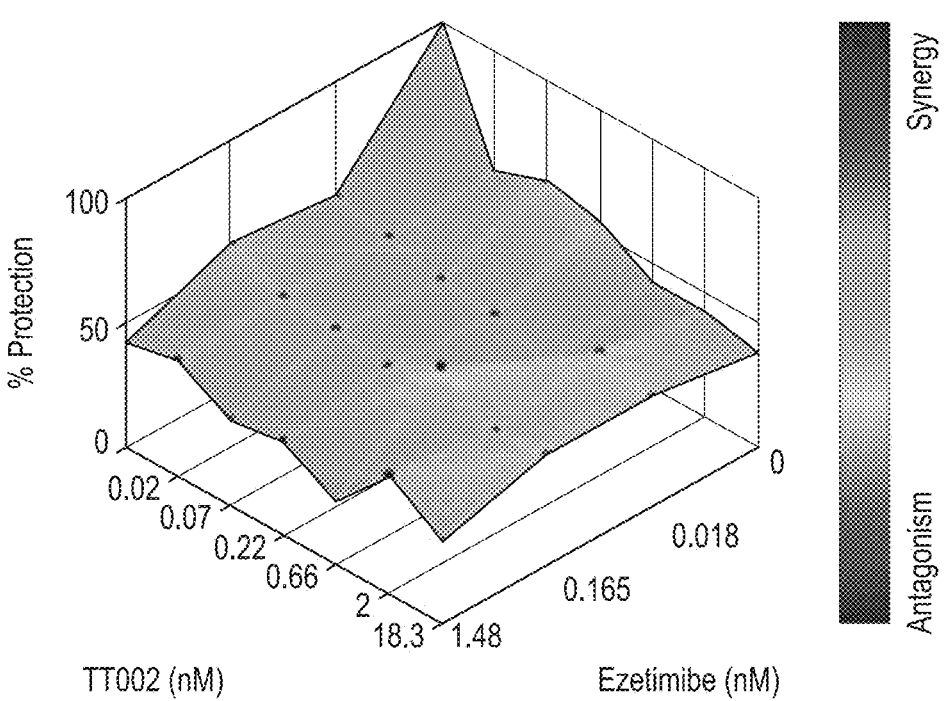
FIG. 6A-6B shows Niclosamide and ezetimibe exhibit synergistic/additive otoprotection. A three-dimensional contour plot (A) showing dose response of neuromast hair cell protection in zebrafish treated with varying concentrations of niclosamide (TT002) and ezetimibe mapped to synergy distribution. Additionally, Loewe synergy and antagonism scores (B) calculated for each combination of doses indicate highest synergistic activity when 0.66 nM niclosamide (TT002) is combined with 1.48 µM ezetimibe (n=5 per group). Other dose combinations showing synergy are shown in dark blue boxes. Dose combinations with scores of 0 and 1 show additive effect. *P<5×10–2; P<10–3, *P<10–4 versus control fish, One-sample t-test run by the Combenefit software44. Data is shown as mean±standard deviation. Ezetimibe is a cholesterol absorption inhibitor.
Figure 6B:
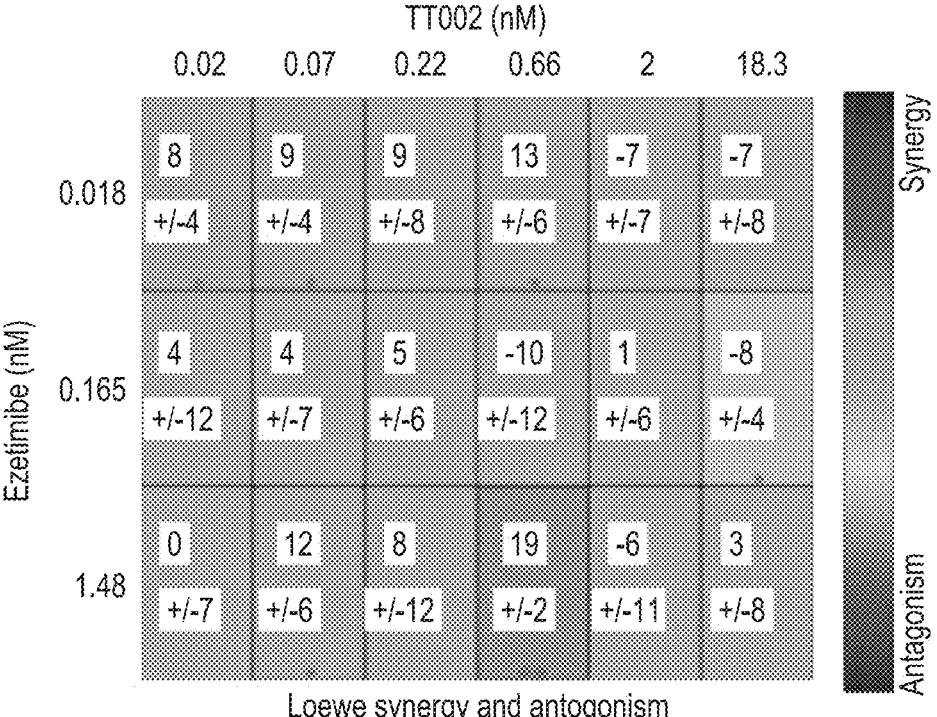

Now referring to FIGS. 6A-6B, 5 dpf zebrafish were either incubated with vehicle (DMSO), cisplatin alone at 300 μM concentration, cisplatin and ezetimibe (0.002 μM to 13.3 μM), cisplatin and niclosamide (0.02 nM to 18.3 nM), or cisplatin and combination ezetimibe/niclosamide. After 6 hours, animals were transferred to fresh water for 1 hour and then sacrificed and processed for immunohistochemistry and HC count as described above. To further elucidate whether Niclosamide, synergizes with Nrf2 activators to protect zebrafish HCs from Cisplatin damage, we tested the extent of HC damage in presence of Niclosamide and a Nrf2 activator, ezetimibe.

Now referring to FIG. 6A, Niclosamide and ezetimibe show synergistic/additive otoprotection. A three-dimensional contour plot (A) showing dose response of neuromast hair cell protection in zebrafish treated with varying concentrations of niclosamide and ezetimibe mapped to synergy distribution. Additionally, Loewe synergy and antagonism scores (B) calculated for each combination of doses indicate highest synergistic activity when 0.66 nM niclosamide is combined with 1.48 μM ezetimibe (n=5 per group). Other dose combinations showing synergy are shown in dark blue boxes. Dose combinations with scores of 0 and 1 show additive effect. *P<5×10–2; P<10–3, *P<10–4 versus control fish, One-sample t-test run by the Combenefit software44. Data is shown as mean±standard deviation.

Ezetimibe alone showed higher HC per neuromast counts at 1.48 μM, while Niclosamide alone showed higher counts at concentrations above 2 nM. However, combining both compounds showed significantly higher hair cell counts across a much lower range of doses for both Niclosamide and Ezetimibe (n=5 per group, One Way ANOVA). Zebrafish were treated with combinations of Niclosamide (ranging from 0.02-18.3 nM) and EZ (ranging from 0.0183-13.3 μM).

Additionally to FIGS. 6A-6B, but not shown, 5 dpf zebrafish were incubated for 6 hours with vehicle, niclosamide (2 nM to 1.48 μM) and the nrf2 pathway activator dimethyl maleate (DEM) as a positive control, in order to evaluate the effect of niclosamide on ggcsh, a nrf2 downstream target. Ggcsh was previously validated as a Nrf2 downstream target in zebrafish. (Sheets, 2017). Following incubation, the total RNA was isolated from whole fish and processed to measure the induced expression of nrf2 downstream gene ggcsh. Expression of ggcsh is significantly lowered in zebrafish treated with Niclosamide ranging from 0.002-1.48 μM (n=5 per group, One Way ANOVA). Additionally, Nrf2a morpholinos morphlinos were prepared, followed by incubation of the zebrafish morphants with cisplatin and/or niclosamide. Zebrafish eggs were injected with 4.5 ng of scrambled morpholino or nrf2a morpholino (5'-CATTTCAATCTCCATCATGTCTCAG SEQ NO: 1). At 3 dpf non-injected and morphant animals were exposed to vehicle, cisplatin (300 μM), cisplatin+niclosamide 18.3 nM or niclosamide alone for 6 hours. Following 1-hour recovery, animals were fixed and processed for immunohistochemistry. Nrf2a KD was confirmed by analyzing expression of Glutathione S-transferase P1 (gstp1), a downstream target, due to lack of proper antibody to detect Nrf2 protein in zebrafish. Zebrafish morpholino demonstrated that nrf2a knock-down reduces Niclosamide's otoprotective effects. Non-injected and scrambled control zebrafish showed significantly higher hair cell number after cotreatment with cisplatin and Niclosamide, while nrf2a knock-down zebrafish showed similar hair cell counts as cisplatin-only treated zebrafish (n=5 per group, One Way ANOVA). These results demonstrate that niclosamide protection against cisplatin ototoxicity requires Nrf2 in zebrafish.

Figure 7:
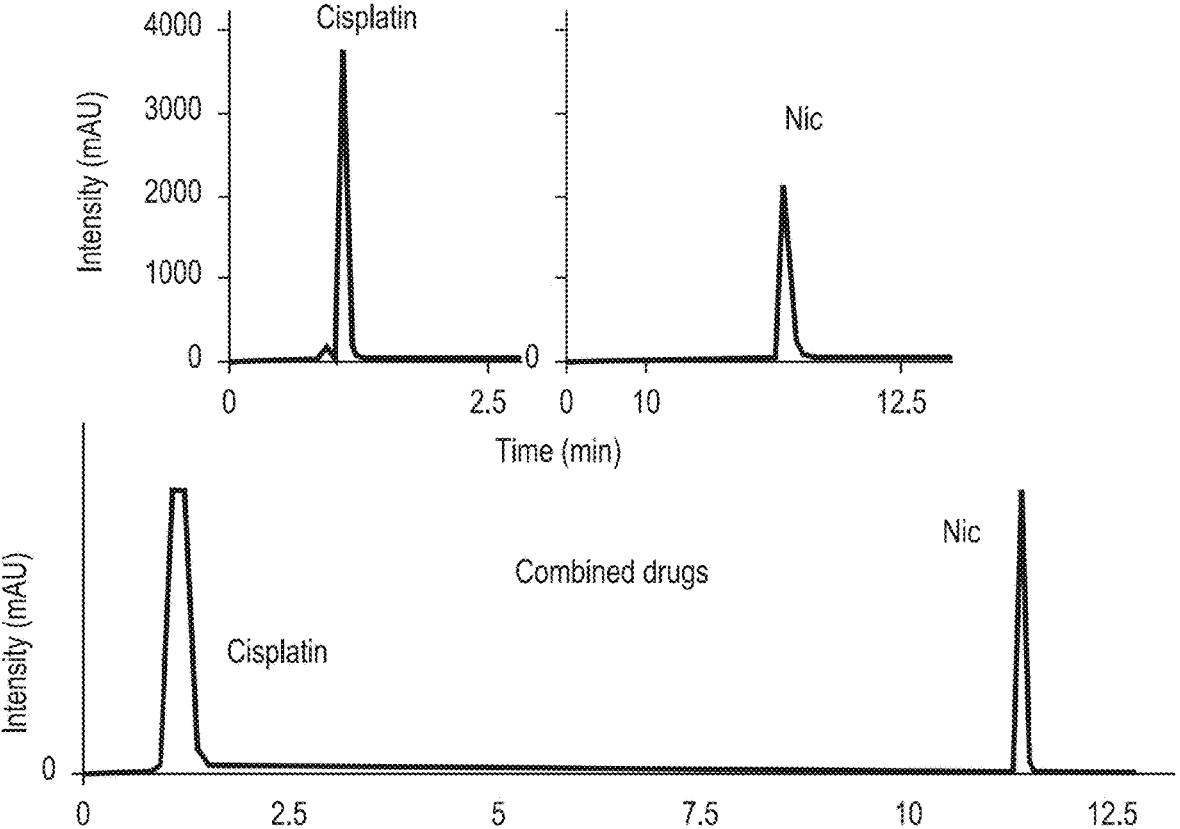
FIG. 7 shows HPLC analysis of the interaction between Niclosamide and Cisplatin in vitro.

Now referring to FIG. 7, HPLC analysis demonstrates no interaction between Niclosamide, and Cisplatin: Drug-drug interactions though chemical binding can have negative impact on cancer treatment. A simple explanation of Niclosamide's protection against CIHL is that it directly inactivates Cisplatin, similar to several otoprotectants in clinical trials (STS, ebselen, etc.). To investigate any possible interaction between Niclosamide and Cisplatin, we developed an HPLC method in vitro. The method may use the following: HPLC: Shimadzu Prominence-i LC-2030C, column: Agilent Eclipse Plus C18, PN-959961-902, 5% ACN, 95% water:

0-2 min; continuous increase of ACN to 95%: 2-12 min; hold at 95% ACN: 12-17 min; continuous decrease of ACN to 5%: 17-20 min, flow rate: 1 mL/min; Temperature 37° C., run time: 20 min. Additional parts of the method may use a stock solution of 1 mg/ml prepared in suitable solvent and mixed to create a ratio of cisplatin and niclosamide at 1:1 and 1:10 in the final injecting solution, along with the pure cisplatin and niclosamide. The results demonstrate no interaction between Niclosamide and Cisplatin (absence of third peak) at several dose ratios of Niclosamide and Cisplatin. Our in vitro results are consistent with its synergistic interaction with Cisplatin in RCC xenograft models and its protection against noise injury.

Figure 8:
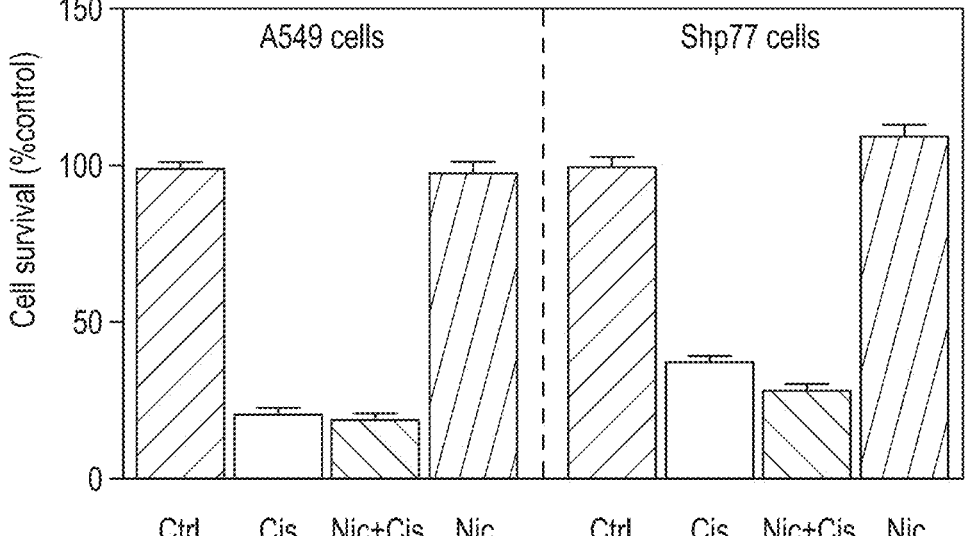
FIG. 8 shows survival of the non-small cell lung carcinoma cell line SHP77 and the small cell lung carcinoma cell line A549 when incubated with or without Cisplatin and 10 nM of Niclosamide. Niclosamide, alone did not affect Cisplatin-tumor killing activity.

Now referring to FIG. 8, In vitro model of non-small cell lung carcinoma cell line SHP77 and small cell lung carcinoma cell line A549 incubated with or without Cisplatin and 10 nM of Niclosamide. Cells were maintained in culture with the aid of Matrigel as previously described in Kelley and Driver, Curr. Protoc. Neurosci. Ch.(4); Unit(4); 34.1-10 (2010). After cells had been in culture for 1 d, growth medium DMEM (12430-054; GIB CO Life Technologies, with 1% FBS [16000-044; GIB CO Life Technologies] and 50 μg/ml ampicillin) with or without test compounds may be added for preincubation for 1 hr. at 37° C. in 5% Co2, and may be followed by incubation with 50 μM Cisplatin (479306; Sigma-Aldrich) with or without the test compound in growth medium for 24 hr. at 37° C. A Cisplatin concentration of 50 μM may be used for the explant assay due to its consistent showing of decreases outer hair cells by about −40% in the mouse cochlea after 24 hours. Cochlea may be fixed in 4% PFA and stained for actin with Alex Fluor 568 phalloidin to determine the viability of the HCs. Cochlea may also be stained by DAPI, FM1-43 dye uptake, and immunohistochemical staining for known HC markers (including parvalbumin and myosin 7a. Cochlea may be imaged by confocal microscopy. Two 160-μm regions from middle turns may be photographed, and the number of intact HCs can be counted.

For comparison of the explant assays of Niclosamide, known benchmark compound kenpaullone, may be tested under similar procedures as above. The following modifications may be used in the comparison assays: (1) filters (Millicell, PICM03050; Millipore) instead of Matrigel in 6-well culture plates with 1 ml medium solution both inside and out the filter; (2) the P3 FVB mouse strain; and (3) Cisplatin doses of 150 μM that consistently show the loss of about ~40% outer hair cells within 24 hr., based on dose responses of Cisplatin at 50, 100, 150, and 200 μM. Teitz et al., J. Exp. Med. 215(4):1187-1203 (2018). Niclosamide, and Cisplatin cotreatment may be further characterized by treating explants with varying about of Cisplatin at varying time periods. For example, 150 μM Cisplatin may be used with or without the test compounds and measurements described above may be taken after 48 hr. incubation.

Cisplatin washout experiments may be used to confirm CIHL and test compounds effect in mitigating such response. For instance, Cisplatin at the various concentrations may be removed after 90 min of incubation (an estimated time that Cisplatin stays in the inner ear in vivo after IP injection) and measurements described above may be taken after the varying incubation periods.

Figure 9A:
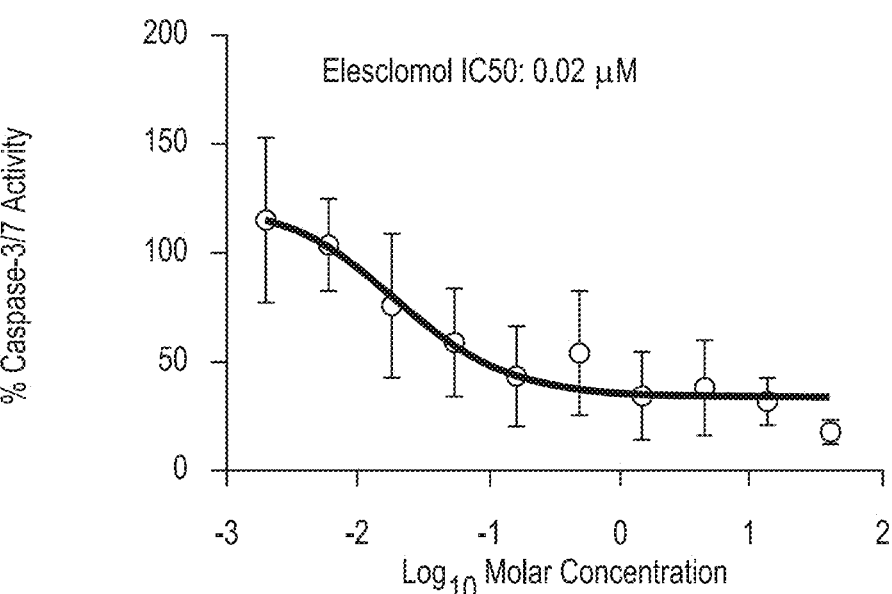
FIG. 9A-9B shows the dose response curve of Elesclomol with Cisplatin exposure. Caspase3-7 activity was measured in HEI-OC1 cells treated with Cisplatin (50 µM). Raw caspase reads were normalized to caspase activity in cells treated with Cisplatin/DMSO and cells treated with 1% DMSO. Elesclomol was shown to reduce caspase activity to comparable levels as control cells at a dose of 40 µM. Data are shown as mean±standard error (n=3 wells per treatment). *P<0.05 (One Way ANOVA). B) Highest level of protection in zebrafish treated with Cisplatin and Elesclomol quantified by neuromast count hair cell count. Quantification of the HCs at S03 (supraorbital line neuromast) and 01-2 (Otic line neuromasts) revealed significantly reduced Cisplatin damage in zebrafish HCs pretreated with 0.165, 1.48, and 13.3 µM Elesclomol.

Now referring to FIG. 9A, Elesclomol protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with Elesclomol reached 20% caspase activity at a dosage of ~40 μM. Additionally, Niclosamide, had a relatively low calculated $IC_{50}$ of 0.02 μM. FIG. 9A.

Figure 9B:
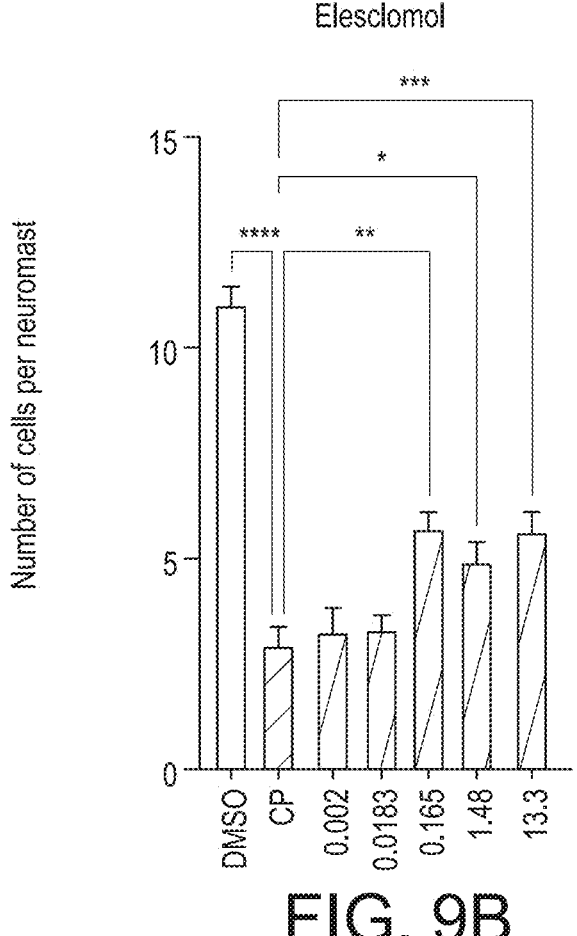

Now referring to FIG. 9B, Elesclomol protects against Cisplatin ototoxicity across multiple doses in zebrafish (n=5-8 per group, One Way ANOVA). *P<0.05, data are shown as mean±standard error (n=5 per group). *P<0.05, data shown as mean±standard error in all panel. Zebrafish were incubated with Elesclomol at 0.002, 0.018, 0.165, 1.48, and 13.3 μM for 1 hour followed by co-incubation with 400 μM Cisplatin for 4 hours. At doses of 0.165, 1.48, and 13.3 μM Elesclomol showed protection against CIHL.

Figure 10A:
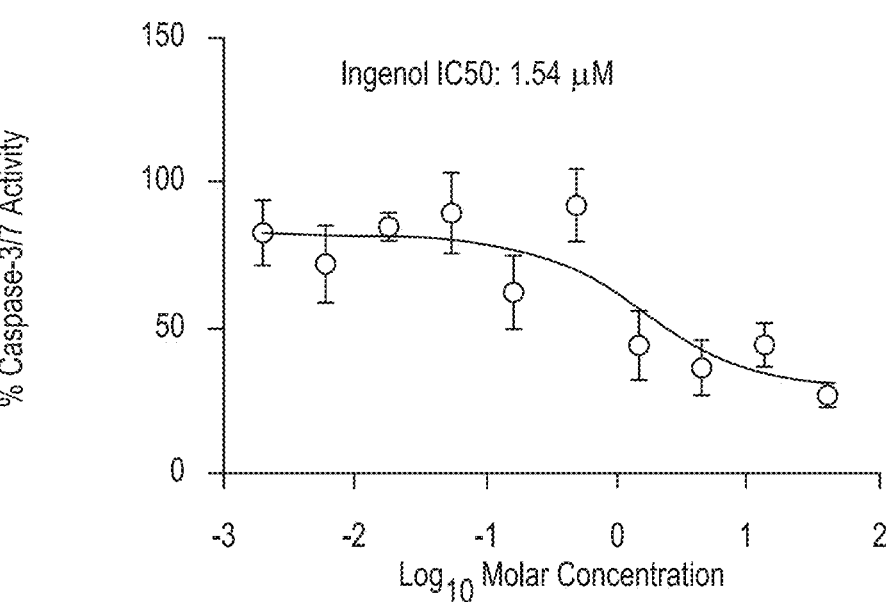
FIG. 10A-10B shows the dose response curve of Ingenol with Cisplatin exposure. Caspase3-7 activity was measured in HEI-OC1 cells treated with Cisplatin (50 µM). Raw caspase reads were normalized to caspase activity in cells treated with Cisplatin/DMSO and cells treated with 1% DMSO. Elesclomol was shown to reduce caspase activity to comparable levels as control cells at a dose of 40 µM. Data are shown as mean±standard error (n=3 wells per treatment). *P<0.05 (One Way ANOVA). B) Highest level of protection in zebrafish treated with Cisplatin and Ingenol quantified by neuromast count hair cell count. Quantification of the HCs at S03 (supraorbital line neuromast) and 01-2 (Otic line neuromasts) revealed significantly reduced Cisplatin damage in zebrafish HCs pretreated with 0.002, 0.0183, 0.165, 1.48 µM Ingenol.

Now referring to FIG. 10A, Ingenol protects against CIHL. Caspase activity was measured using Caspase-Glo 3/7 assay and then the results were calculated as percentage of protection as an indicator of cell survival/viability. Percent protection for each compound at the tested dosages were then plotted to show dose response curves, and $IC_{50}$s were calculated. HEI-OC1 cells treated with Ingenol reached 30% caspase activity at a dosage of ~40 μM. Additionally, Ingenol had a relatively low calculated $IC_{50}$ of 1.54 μM. FIG. 10A.

Figure 10B:
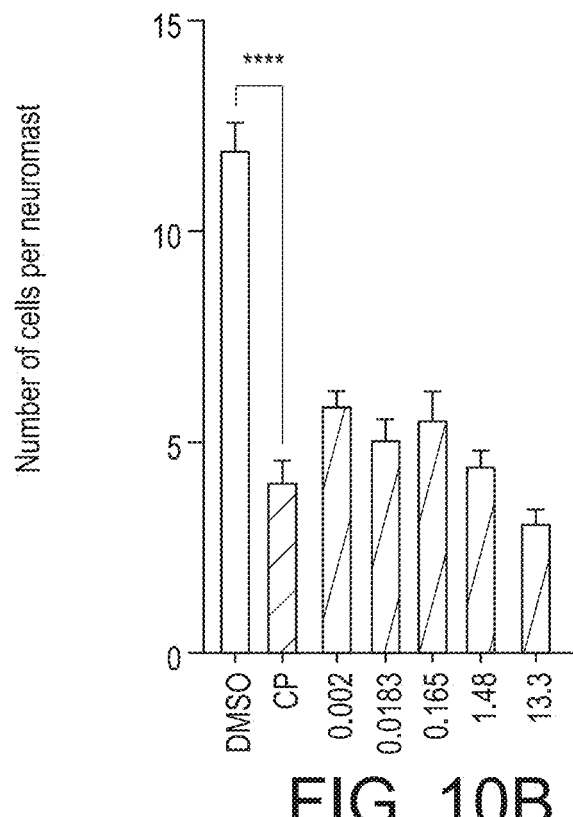

Now referring to FIG. 10B, Ingenol protects against Cisplatin ototoxicity across multiple doses in zebrafish (n=5-8 per group, One Way ANOVA). *P<0.05, data are shown as mean±standard error (n=5 per group). *P<0.05, data shown as mean±standard error in all panels. Zebrafish were incubated with Ingenol at 0.002, 0.018, 0.165, 1.48, and 13.3 μM for 1 hour followed by co-incubation with 400 μM Cisplatin for 4 hours. At doses of 0.002, 0.0183, 0.165, and 1.48 μM Ingenol showed protection against CIHL.

All publications, patents and patent applications mentioned in this specification are herein incorporated by reference to the same extent as if each individual publication, patent, or patent application was specifically and individually indicated to be incorporated by reference.

1. Chen X, Wu Y, Dong H, Zhang C Y, Zhang Y. Platinum-based agents for individualized cancer treatment. Curr Mol Med 2013; 13:1603-12. PMID: 24206132.

2. Magnes T, Egle A, Greil R, Melchardt T. Update on squamous cell carcinoma of the head and neck: ASCO annual meeting 2017. Memo 2017; 10:220-3. PMID: 29250200.

3. Sheth S, Mukherjea D, Rybak L P, Ramkumar V. Mechanisms of Cisplatin-Induced Ototoxicity and Otoprotection. Front Cell Neurosci 2017; 11:338. PMID: 29163050.

4. Dickey D T, Wu Y J, Muldoon L L, Neuwelt E A. Protection against Cisplatin-induced toxicities by N-acetylcysteine and sodium thiosulfate as assessed at the molecular, cellular, and in vivo levels. J Pharmacol Exp Ther 2005; 314:1052-8. PMID: 15951398.

5. So H S, Park C, Kim H J, et al. Protective effect of T-type calcium channel blocker flunarizine on Cisplatin-induced death of auditory cells. Hear Res 2005; 204:127-39. PMID: 15925198.

6. Teitz T, Fang J, Goktug A N, et al. CDK2 inhibitors as candidate therapeutics for Cisplatin- and noise-induced hearing loss. J Exp Med 2018; 215:1187-203. PMID: 29514916.

7. Baker T G, Roy S, Brandon C S, et al. Heat shock protein-mediated protection against Cisplatin-induced hair cell death. J Assoc Res Otolaryngol 2015; 16:67-80. PMID: 25261194.

8. Kim S J, Park C, Han A L, et al. Ebselen attenuates Cisplatin-induced ROS generation through Nrf2 activation in auditory cells. Hear Res 2009; 251:70-82. PMID: 19286452.

9. Ryals M, Pak K, Jalota R, Kurabi A, Ryan A F. A kinase inhibitor library screen identifies novel enzymes involved in ototoxic damage to the murine organ of Corti. PLoS One 2017; 12:e0186001. PMID: 29049311.

10. Kitcher S R, Kirkwood N K, Camci E D, et al. ORC-13661 protects sensory hair cells from aminoglycoside and Cisplatin ototoxicity. JCI Insight 2019; 4. PMID: 31391343.

11. Brock P R, Maibach R, Childs M, et al. Sodium Thiosulfate for Protection from Cisplatin-Induced Hearing Loss. N Engl J Med 2018; 378:2376-85. PMID: 29924955.

12. Chen W, Mook R A, Jr., Premont R T, Wang J. Niclosamide, Beyond an antihelminthic drug. Cell Signal 2018; 41:89-96. PMID: 28389414.

13. Zhao J, He Q, Gong Z, Chen S, Cui L. Niclosamide, suppresses renal cell carcinoma by inhibiting Wnt/beta-catenin and inducing mitochondrial dysfunctions. Springerplus 2016; 5:1436. PMID: 27652012.

14. Sack U, Walther W, Scudiero D, et al. Novel effect of antihelminthic Niclosamide, on S100A4-mediated metastatic progression in colon cancer. J Natl Cancer Inst 2011; 103:1018-36. PMID: 21685359.

15. Park S Y, Kim J Y, Choi J H, et al. Inhibition of LEF1-Mediated DCLK1 by Niclosamide, Attenuates Colorectal Cancer Stemness. Clin Cancer Res 2019; 25:1415-29. PMID: 30446587.

16. Lamb J, Crawford E D, Peck D, et al. The Connectivity Map: using gene-expression signatures to connect small molecules, genes, and disease. Science 2006; 313:1929-35. PMID: 17008526.

17. Musa A, Ghoraie L S, Zhang S D, et al. A review of connectivity map and computational approaches in pharmacogenomics. Brief Bioinform 2018; 19:506-23. PMID: 28069634.

18. Duan Q, Reid S P, Clark N R, et al. L1000CDS(2): LINCS L1000 characteristic direction signatures search engine. NPJ Syst Biol Appl 2016; 2. PMID: 28413689.

19. Caroli J, Sorrentino G, Forcato M, Del Sal G, Bicciato S. GDA, a web-based tool for Genomics and Drugs integrated analysis. Nucleic Acids Res 2018; 46:W148-W56. PMID: 29800349.

20. Hazlitt R A, Teitz T, Bonga J D, et al. Development of Second-Generation CDK2 Inhibitors for the Prevention of Cisplatin-Induced Hearing Loss. J Med Chem 2018; 61:7700-9. PMID: 30091915.

21. Kalinec G M, Webster P, Lim D J, Kalinec F. A cochlear cell line as an in vitro system for drug ototoxicity screening. Audiol Neurootol 2003; 8:177-89. PMID: 12811000.

22. Ou H C, Santos F, Raible D W, Simon J A, Rubel E W. Drug screening for hearing loss: using the zebrafish lateral line to screen for drugs that prevent and cause hearing loss. Drug Discov Today 2010; 15:265-71. PMID: 20096805.

23. Vlasits A L, Simon J A, Raible D W, Rubel E W, Owens K N. Screen of FDA-approved drug library reveals compounds that protect hair cells from aminoglycosides and Cisplatin. Hear Res 2012; 294:153-65. PMID: 22967486.

24. Rocha-Sanchez S M, Fuson O, Tarang S, et al. Quinoxaline protects zebrafish lateral line hair cells from Cisplatin and aminoglycosides damage. Sci Rep 2018; 8:15119. PMID: 30310154.

25. Xiao T, Roeser T, Staub W, Baier H. A GFP-based genetic screen reveals mutations that disrupt the architecture of the zebrafish retinotectal projection. Development 2005; 132:2955-67. PMID: 15930106.

26. Gregory M A, D'Alessandro A, Alvarez-Calderon F, et al. ATM/G6PD-driven redox metabolism promotes FLT3 inhibitor resistance in acute myeloid leukemia. Proc Natl Acad Sci USA 2016; 113:E6669-E78. PMID: 27791036.

27. Rymal K S, Chambliss O L, Bond M D, Smith D A. Squash Containing Toxic Cucurbitacin Compounds Occurring in California and Alabama. J Food Prot 1984; 47:270-1. PMID: 30921968.

28. Breglio A M, Rusheen A E, Shide E D, et al. Cisplatin is retained in the cochlea indefinitely following chemotherapy. Nat Commun 2017; 8:1654. PMID: 29162831.

29. Osada T, Chen M, Yang X Y, et al. Antihelminth compound Niclosamide, downregulates Wnt signaling and elicits antitumor responses in tumors with activating APC mutations. Cancer Res 2011; 71:4172-82. PMID: 21531761.

30. Bhagat H A, Compton S A, Musso D L, et al. N-substituted phenylbenzamides of the Niclosamide, chemotype attenuate obesity related changes in high fat diet fed mice. PLoS One 2018; 13:e0204605. PMID: 30359371.

31. Burock S, Daum S, Keilholz U, Neumann K, Walther W, Stein U. Phase II trial to investigate the safety and efficacy of orally applied Niclosamide, in patients with metachronous or sychronous metastases of a colorectal cancer progressing after therapy: the NIKOLO trial. BMC Cancer 2018; 18:297. PMID: 29544454.

32. Layman W S, Williams D M, Dearman J A, Sauceda M A, Zuo J. Histone deacetylase inhibition protects hearing against acute ototoxicity by activating the Nf-kappaB pathway. Cell Death Discov 2015; 1. PMID: 26279947.

33. Yu Y, Hu B, Bao J, et al. Otoprotective Effects of *Stephania tetrandra* S. Moore Herb Isolate against Acoustic Trauma. J Assoc Res Otolaryngol 2018; 19:653-68. PMID: 30187298.

34. Fernandez K, Wafa T, Fitzgerald T S, Cunningham L L. An optimized, clinically relevant mouse model of Cisplatin-induced ototoxicity. Hear Res 2019; 375:66-74. PMID: 30827780.

35. Liu H, Li Y, Chen L, et al. Organ of *Corti* and Stria Vascularis: Is there an Interdependence for Survival? PLoS One 2016; 11:e0168953. PMID: 28030585.

36. Huang L, Yang M, Yuan Y, Li X, Kuang E. Niclosamide, inhibits lytic replication of Epstein-Barr virus by disrupting mTOR activation. Antiviral Res 2017; 138:68-78. PMID: 27939840.

37. Peng J, Sun B F, Chen C Y, et al. Single-cell RNA-seq highlights intra-tumoral heterogeneity and malignant progression in pancreatic ductal adenocarcinoma. Cell Res 2019; 29:725-38. PMID: 31273297.

38. Yamashita T, Zheng F, Finkelstein D, et al. High-resolution transcriptional dissection of in vivo Atoh1-mediated hair cell conversion in mature *cochleae* identifies Isl1 as a co-reprogramming factor. PLoS Genet 2018; 14:e1007552. PMID: 30063705.

39. Li S F, Tang J J, Chen J, et al. Regulation of bone formation by baicalein via the mTORC1 pathway. Drug Des Devel Ther 2015; 9:5169-83. PMID: 26392752.

40. Salehi P, Ge M X, Gundimeda U, et al. Role of Neuropilin-1/Semaphorin-3A signaling in the functional and morphological integrity of the cochlea. PLoS Genet 2017; 13:e1007048. PMID: 29059194.

41. Salehi P, Myint A, Kim Y J, et al. Genome-Wide Association Analysis Identifies Dcc as an Essential Factor in the Innervation of the Peripheral Vestibular System in Inbred Mice. J Assoc Res Otolaryngol 2016; 17:417-31. PMID: 27539716.

42. Zhao S J, Kong F Q, Jie J, et al. Macrophage MSR1 promotes BMSC osteogenic differentiation and M2-like polarization by activating PI3K/AKT/GSK3beta/beta-catenin pathway. Theranostics 2020; 10:17-35. PMID: 31903103.

43. Tian Y, Shen L, Li F, Yang J, Wan X, Ouyang M. Silencing of RHEB inhibits cell proliferation and promotes apoptosis in colorectal cancer cells via inhibition of the mTOR signaling pathway. J Cell Physiol 2020; 235: 442-53. PMID: 31332784.

44. Salehi P, Nelson C N, Chen Y, et al. Detection of single mRNAs in individual cells of the auditory system. Hear Res 2018; 367:88-96. PMID: 30071403.

45. Wieland A, Trageser D, Gogolok S, et al. Anticancer effects of Niclosamide, in human glioblastoma. Clin Cancer Res 2013; 19:4124-36. PMID: 23908450.

46. Jia S, Yang S, Guo W, He D Z. Fate of mammalian cochlear hair cells and stereocilia after loss of the stereocilia. J Neurosci 2009; 29:15277-85. PMID: 19955380.

47. Madan E, Parker T M, Bauer M R, et al. The curcumin analog HO-3867 selectively kills cancer cells by converting mutant p53 protein to transcriptionally active wildtype p53. J Biol Chem 2018; 293:4262-76. PMID: 29382728.

48. Di Veroli G Y, Fornari C, Wang D, Mollard S, Bramhall J L, Richards F M, Jodrell D I. 2016. Combenefit: an interactive platform for the analysis and visualization of drug combinations. Bioinformatics 32:2866-2868. doi: 10.1093/bioinformatics/btw230. CrossRefPubMed-Google Scholar 49. Loewe S. 1953. The problem of synergism and antagonism of combined drugs. Arzneimittelforschung 3:285-290. PubMedGoogle Scholar 50. Bliss C. 1939. The toxicity of poisons applied jointly 1. Ann Appl Biol 26:585-615. doi:10.1111/j.1744-7348.1939.tb06990.x.CrossRefWeb of ScienceGoogle Scholar 51. Cerles O, Benoit E, Chereau C, Chouzenoux S, Morin F, Guillaumot M A, Coriat R, Kavian N, Loussier T, Santulli P, Marcellin L, Saidu N E, Weill B, Batteux F, Nicco C. Niclosamide, Inhibits Oxaliplatin Neurotoxicity while Improving Colorectal Cancer Therapeutic Response. Mol Cancer Ther. 2017 February; 16(2):300-311. doi: 10.1158/1535-7163.MCT-16-0326. Epub 2016 Dec. 15. PMID: 27980107.

52. Park J S, Lee Y S, Lee D H, Bae S H. Repositioning of Niclosamide, ethanolamine (NEN), an anthelmintic drug, for the treatment of lipotoxicity. Free Radic. Biol. Med., 137 (2019), pp. 143-157

53. Kujawa S G, Liberman M C. Acceleration of age-related hearing loss by early noise exposure: evidence of a misspent youth. J Neurosci 2006; 26:2115-23. PMID: 16481444.

54. Sheets L. Excessive activation of ionotropic glutamate receptors induces apoptotic hair-cell death independent of afferent and efferent innervation. Sci Rep. 2017 Jan. 23; 7:41102.

55. Caroli J, Sorrentino G, Forcato M, Del Sal G, Bicciato S. GDA, a web-based tool for Genomics and Drugs integrated analysis. Nucleic Acids Res 2018; 46:W148-W56. PMID: 29800349.

56. Kindt K S, Sheets L. Transmission Disrupted: Modeling Auditory Synaptopathy in Zebrafish. Front Cell Dev Biol 2018; 6:114. PMID: 30258843.

While the invention has been described with reference to details of the illustrated embodiments, these details are not intended to limit the scope of the invention as defined in the appended claims. The embodiment of the invention in which exclusive property or privilege is claimed is defined as follows:

The invention claimed is:

1. A method to prevent ear hair cell loss caused by a chemotherapeutic agent comprising: administering to a mammal in need thereof an effective amount of a pharmaceutical composition containing a therapeutically active agent, wherein the therapeutically active agent is Niclos- amide, or a pharmaceutically acceptable salt thereof to prevent ear hair cell loss caused by the administration of the chemotherapeutic agent, wherein the chemotherapeutic agent is Cisplatin.

* * * * *